Figure 1:
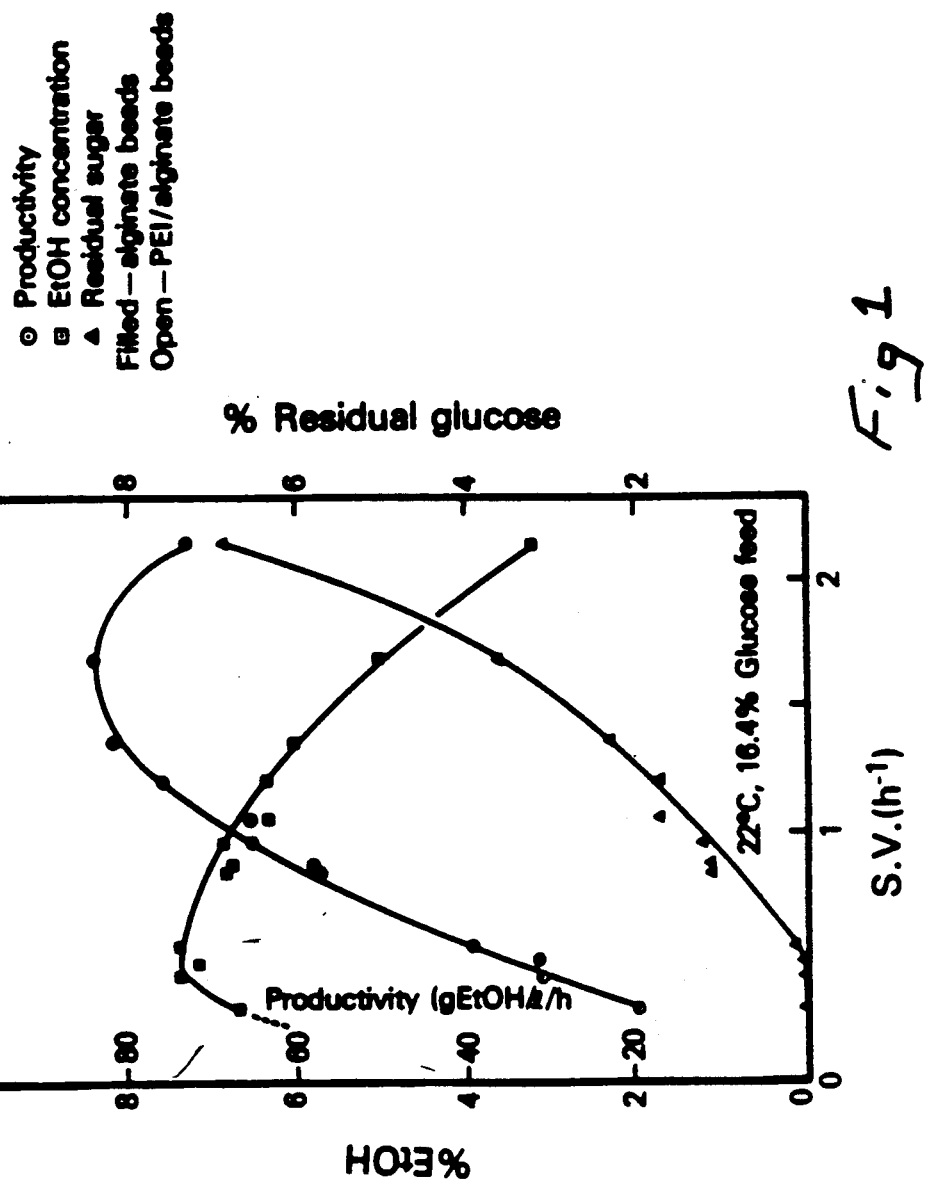

United States Patent [19]

Joung et al.

[11] Patent Number: 4,996,150

[45] Date of Patent: Feb. 26, 1991

[54] BIOCATALYST IMMOBILIZATION IN A GEL OF ANIONIC POLYSACCHARIDE AND CATIONIC POLYMER

[75] Inventors: John J. Joung; Cavit Akin, both of Naperville; Garfield P. Royer, Warrenville, all of Ill.

[73] Assignee: Amoco Corporation, Chicago, Ill.

[21] Appl. No.: 186,062

[22] Filed: Apr. 25, 1988

Related U.S. Application Data

[63] Continuation of Ser. No. 665,750, Oct. 29, 1984, abandoned.

[51] Int. Cl.$^5$ .................. C12P 7/06; C12N 11/10; C12N 11/12; C12N 11/08
[52] U.S. Cl. .................. 435/161; 435/177; 435/178; 435/179; 435/180
[58] Field of Search .............. 435/174, 177, 178, 179, 435/180, 161

[56] References Cited

U.S. PATENT DOCUMENTS

| | | | |
|---|---|---|---|
| 4,138,292 | 2/1979 | Chibata et al. | 435/178 |
| 4,334,027 | 6/1982 | Klein et al. | 435/178 |
| 4,347,320 | 8/1982 | Borglum | 435/178 X |
| 4,391,909 | 7/1983 | Lim | 435/178 |

FOREIGN PATENT DOCUMENTS

| | | | |
|---|---|---|---|
| 0052829 | 6/1982 | European Pat. Off. | |
| 74984 | 4/1984 | Japan | 435/178 |
| 113889 | 6/1984 | Japan | 435/178 |
| 1469072 | 3/1977 | United Kingdom | |
| 2082591 | 3/1982 | United Kingdom | |

OTHER PUBLICATIONS

Mohamed et al., Biotechnology Letters, vol. 4, No. 9, 1982, pp. 611-614.
Chemical Abstracts, vol. 98, No. 12, Mar. 21, 1983, p. 26, Abstract No. 90287z, Columbus, Ohio, U.S., M. Suhaila et al.: "Physical properties of polyethyleneimine-alginate gels", & Biotechnol. Lett. 1982, 4(9), 611–614.
Chemical Abstracts, vol. 95, No. 15, Oct. 12, 1981, p. 513, Abstract No. 130963p, Columbus, Ohio, U.S.; S. Birnbaum et al: "Covalent stabilization of alginate gel for the entrapment of living whole cells", & Biotechnol. Lett. 1981, 3(8), 393-400.
Immobilization of Growing Cells by Polyethyleneimine-Modified Alginate; John J. Joung, Cavit Akin, and G. P. Royer; Applied Biochemistry and Biotechnology; vol. 14, 1987.
A Horizontal Packed-Bed Bioreactor to Reduce $CO_2$ Gas Holdup in the Continuous Production of Ethanol by Immobilized Yeast Cells, Takeshi Shiotani and Tsuneo Yamane; European Journal of Applied Microbiology and Biotechnology (1981) 13: 96-101.

*Primary Examiner*—David M. Naff
*Attorney, Agent, or Firm*—Norville B. Galloway; William H. Magidson; Ralph C. Mehurst

[57] ABSTRACT

An immobilized biocatalyst suitable for fermenting to produce ethanol is prepared by mixing a biocatalyst such as a microorganism with a reaction product of a homogeneous dispersion of an anionic polysaccharide such as alginate and a cationic polymer such as polyethyleneimine, and combining the resultant dispersion with an oil phase to form beads. A surtactant may be present when combining the dispersion with the oil phase. A water soluble-oil insoluble curing powder including a salt of a multivalent cation such as calcium chloride is mixed with the beads in the oil phase to gell and dehydrate the beads and to prevent the beads from adhering to one another until individual bead surfaces become hardened.

19 Claims, 1 Drawing Sheet

BIOCATALYST IMMOBILIZATION IN A GEL OF ANIONIC POLYSACCHARIDE AND CATIONIC POLYMER

This is a continuation of application Ser. No. 665,750, filed Oct. 29, 1984 now abandoned.

BACKGROUND OF THE INVENTION

The present invention pertains to a composition and method for immobilizing microorganisms, catalysts, and enzymes in a gel including an anionic polysaccharide polymer and a cationic polymer, homogeneously dispersed and bonded, to form a matrix structure. In particular, the invention pertains to a method and composition in which an anionic form of alginate, polyethyleneimine, and yeast are homogeneously dispersed in an aqueous system, and thereafter mixed with an oil phase to form beads.

Recent interest has turned to increasing the productivity of bioconversion processes by utilizing "biocatalyst" systems in which cells are immobilized. In the context of the present application, the term "biocatalyst" is understood to mean a biological system including enzymes or whole cellular microorganisms fixed through a macroscopic carrier. As used herein, the term "biocatalytic entity" refers to enzymes or whole cellular microorganisms which are to be incorporated into a biocatalyst. High cell immobilization costs, limited cell service life, loss of catalytic activity and changes in biological behavior of immobilized cells have been major problems which have hindered widespread commercial use of proposed biocatalyst systems.

Currently, there are two techniques for immobilizing cells. One technique involves the use of solid supports. Typically, cells are either cultured or adhered to the surface of the solid support. Wood chips, porous bricks, Rasching rings, PVC flakes, glass fibers, porous glass, and clays have been utilized to obtain surface cultures for the production of ethanol. The use of solid supports has been limited by the problems of cell washout, limited cell loading capability, and a high rate of free cell production in the broth.

Another technique for cell immobilization has been to immobilize cells within a gel matrix usually in the form of beads or pellets. The beads or pellets present a large surface area to mediums in which the beads or pellets are suspended and allow nutrients and reaction products to diffuse into or out of a small cross-sectional area.

A common encapsulation system has utilized polyacrylamide gels. The usefulness of gels made out of polyacrylamide has been limited by the toxicity of the monomer substance and the brittleness of the gels. Hydrogels, derived from marine plants, are considered to be more desirable as a live cell carrier. Hydrogel's inertness, high water holding capacity, permeability, ease of forming and abundance are desirable features for immobilizing cells for bioconversion processes. Examples of hydrogels which have been studied extensively include alginate, carrageenan, and agar.

A typical example of forming gel beads utilizing hydrogels includes mixing an aliquot of yeast slurry in a hydrogel solution at 50° C. The solution is then dripped into a cold organic solvent which reacts with the hydrogel to cause the hydrogel to gel into a bead-like structure. See: K. Toda and M. Shoda, *Biotechnoloy and Bioengineering*, Vol. 17, p. 481 (1975).

M. Wada, J. Kato, and I. Chibata, report in an article entitled "A New Immobilization of Microbial Cells," *European Journal of Applied Microbiology, Biotechnology*, Vol. 8, pp. 241-247 (1979), that beads containing yeast cells have been prepared by dripping a 4% carrageenan solution containing yeast cells into a 2% potassium chloride solution at an ambient temperature. Similarly, T. Shiotani and T. Yamane report in an article entitled "A Horizontal Packed Bed Bioreactor to Reduce $CO_2$ Gas Holdup in the Continuous Production of Ethanol by Immobilized Yeast Cells," *European Journal of Applied Microbiology, Biotechnology*, Vol 1. 13(2) pp. 96-101 (1981) that yeast-alginate beads were prepared from a sodium alginate mixture dripped into calcium chloride solution. I. Veliky and R. Williams report in an article entitled "The Production of Ethanol by Saccharomyces Cervisiae Immobilized in Polycation-Stabilized Calcium Alginate Gels," *Biotech. Lett.*, Vol. 3, pp. 275-280 (1981), the successful immobilization of microorganisms in a calcium alginate matrix which was thereafter further surface treated with polyethyleneimine (hereinafter referred to as PEI).

U.S. Pat. No. 4,355,105 to Lantero entitled "Glutaraldehyde/Polyethyleneimine Immobilization of Whole Microbial Cells" discloses that cells can be immobilized by providing an aqueous medium containing whole cells of a microorganism and adding glutaraldehyde to the aqueous medium to form a reaction product with the microorganism. Thereafter, PEI is added to the aqueous medium to flocculate the reaction product. The reaction product is recovered from the aqueous medium as a cake or pellet which can be further processed into particles or other forms.

U.S. Pat. No. 4,347,320 to Borglum entitled "Immobilization of Microorganisms in Gelled Carrageenan" discloses a method of immobilizing microorganisms by mixing the microorganisms with an aqueous solution of kappa-carrageenan. The microorganisms and kappa-carrageenan are gelled by forming droplets through a nozzle and contacting the droplets with an aqueous solution containing a gelling agent including PEI. The resultant beads have a surface skin of PEI.

Suhaila and Salleh, in an article entitled "Physical Properties of Polyethyleneimine-Alginate Gels," *Biotechnology Letters*, Vol. 4, No. 9, pp. 66-614 (1982) discuss the properties of PEI-propylene glycol alginate gels as compared to gelatin-propylene glycol alginate gels (hereinafter propylene glycol alginate will be referred to as PGA). The authors found that PEI-PGA gels are much more brittle than gelatin-PGA gels but maintain their integrity to a greater extent in acidic conditions and are stable to heat and freezing. While the authors suggest that PEI-PGA gels may be useful for enzyme cell immobilization within certain limitations inherent in the brittle PEI-PGA structure, there is no disclosure of an anionic polysaccharide and a cationic polymer homogeneously dispersed and bonded to form a matrix.

An article in *Newswatch*, p. 3, Mar. 17, 1984, entitled "Crah Chitosan Microbeads Entrap Cells in One Step, Challenge Damon 'Encapcel'," reports that Chokyun Rha of the Massachusetts Institute of Technology has produced globular spheres of 10 microns to 5 millimeters in size with controlled porosity using chitosan (a dissolved deacetylated chitin) and alginate. The article further reports that cells or enzymes are suspended in a cationic chitosan solution. Droplets of the cell-chitosan mixture are added to an anionic solution of alginate or another polymer to form membranes which encapsulate a volume of the liquid chitosan-cell mixture. The membranes can be strengthened by cross-linking with divalent ions or additional polymer layers. The capsules can withstand a 2,000-G force and undergo deformations of up to 90% without rupture.

To the best of our knowledge, these proposals have not led to biocatalytic systems utilizing beads having sufficient strength and resiliency while capable of maintaining cell viability. Materials such as glutaraldehyde and PEI have not found widespread use in biocatalytic gel matrix systems. Generally, the PEI and glutaraldehyde in solution have fungicidal and bactericidal action which greatly limits their use for incorporation into matrixes. Specifically, PEI is ionic in solution and may cause cell lysis. Accordingly, one would not predict that homogeneous incorporation of PEI within a matrix system would result in live cell systems having catalytic activity.

In the past, PEI has been used primarily to impart rigidity to beads. The PEI would be applied to the bead structure as a coating or skin such that the toxic effects of PEI would not damage the biocatalyst. Rigid or hard beads were considered better suited for packing in a column. However, rigid or hardened beads are unable to accommodate cellular growth and are incapable of venting gaseous metabolic by-products. In fermentation processes which extend over a long period of time, rigid bead structures rupture and release the biocatalyst from the gel matrix.

The prior art does not suggest a practical means for obtaining beads having a predetermined substantially uniform size. Bead size is an important consideration in biocatalytic systems. Cells incorporated within the interior of large beads cannot proliferate or contribute to fermentation processes due to the cell's inability to obtain necessary nutrients through the matrix structure. Only cells incorporated near the surface of the gel's matrix proliferate and actively contribute to fermentation processes.

Gel matrixes comprising hydrogel which utilize calcium for the formation of a cross-linking structure eventually dissolve releasing the biocatalyst. Microorganisms generally utilize the calcium within the matrix structure for their own purposes, and calcium is released from the matrix structure as part of an ongoing release upon dissolution of the bead components within an aqueous medium.

DESCRIPTION OF THE INVENTION

It is an object of the present invention to present an improved biocatalyst system which is capable of continuous bioconversion processes on a large scale.

Other objects, features, and advantages of the present invention will be apparent to those skilled in the art from the following more detailed description of preferred embodiments, which exemplifies the present invention.

Briefly, an embodiment of the present invention includes a biocatalytic system comprising a dispersion of a biocatalytic entity within the reaction product of a homogeneous mixture of an anionic polysaccharide polymer and a cationic polymer.

Preferred cationic polymers include polyalkene amines or imines and, in particular, PEI. Other cationic polymers may include, by way of example without limitation, polyepihalohydrin amines and imines, polypropylene amines and imines, polylysine, polycationic polypeptides and others. Surprisingly and unexpectedly, cationic polymers such as PEI, which are normally toxic to fungi and bacteria, are neutralized and rendered non-toxic to yeast when uniformly dispersed with an anionic polysaccharide polymer such as sodium alginate. Yeast incorporated within an alginate-PEI matrix remains viable. It is further believed that the PEI incorporated within the PEI alginate matrix contributes to asepsis of the reactor vessel reducing the possibility of contamination.

Preferred anionic polysaccharide polymers include alkali metal or ammonium salts of alginate such as sodium alginate, potassium alginate, and ammonium alginate. Other anionic polysaccharide polymers may include kappa-carrageenan, agar carboxymethylcellulose and generally any polysaccharide containing sulfonic or carboxylic groups.

A preferred embodiment includes a biocatalytic entity in the form of a yeast. Other biocatalytic entities may include, by way of example without limitation, molds and algae. The present invention may have particular commercial importance for yeast including Saccharomyces cerevisiae, Kluyveromyces fragilis, Candida utilis, Saccharomycopsis lipolytica, Eremothecium ashbyi and others. Molds of interest include Pennicillium roguefortii, Pennicillium camembertii, Penicillium chrysogenum, Aspergillus oryzae, Aspergillus niger, Rhizopus nigricans, Mucor, Monascus purpurea, Trichoderma reesii, Endothia parasitica, Cephalosporium acremonium, Blakeslea trispora and others.

A further embodiment of the present invention includes a method of making a biocatalytic system which includes the step of preparing a mixture of a biocatalytic entity with the reaction product of a homogeneous mixture of an anionic polysaccharide polymer and a cationic polymer, to form a polymer-biocatalyst dispersion. Next, the polymer-biocatalyst dispersion is mixed with an oil phase to form beads. Preferably, the polymer-biocatalyst dispersion is mixed with an oil phase in the presence of surfactants which include water insoluble surfactants and water soluble surfactants. The relative concentrations of the surfactants determine the size of the beads. The present method produces beads of uniform size and shape.

The beads are gelled and dehydrated by subjecting the beads to a water soluble-oil insoluble curing powder. Preferably, the powder includes a salt of a multivalent cation, and, in particular, calcium chloride or aluminum sulfate. However, other multivalent cationic salts of Group II or III metals may also be used with due consideration of their potential toxicity to microorganisms.

The present invention is well-suited for continuous ethanol or organic acid production in a column reactor. The present invention for producing ethanol obtained a production rate of 86 grams per liter per hour (g/l/h) as applied to glucose conversion in a column reactor. In a column reactor, the ethanol concentration of the product was 5% after a single pass at 22° C. The present invention provides rapid ethanol production, with a rate 80-fold faster than the rate of a conventional batch fermenter. A 16.4% glucose feed was nearly completely converted to ethanol with a 47% yield based on a glucose feed at a space velocity of 0.53 $h^{-1}$. Thus, the present invention permits the production of ethanol at 92% of the theoretical yield.

In embodiments of the present invention employing PEI, maintenance of an aseptic operation was possible for a prolonged period without sterilizing the reactor system due to the bactericidal action of PEI. Embodiments of the present invention, including alginate-PEI-yeast beads, could withstand vigorous gas action in a digestive environment of an alcohol fermenter. In comparison, beads made of alginate without PEI easily became ruptured, deformed, and partially liquefied, releasing the biocatalyst.

Whereas much of the prior art has suggested means for hardening and strengthening biocatalytic beads, the present invention includes beads having substantial resiliency. Surprisingly and unexpectedly, the incorporation of PEI throughout the matrix structure provides beads which can accommodate expansion due to yeast growth within the matrix and allows venting of metabolic gases. In the past, PEI has been used as a hardening agent. Matrixes incorporating PEI have been described as rigid and brittle in the past.

The present invention includes an alginate-PEI-yeast matrix in a bead-like structure which allows for an increase in weight of an individual bead of 600% and an increase in diameter of about 90%. The carrier matrix of the present invention is capable of withstanding phosphate and high concentrations of ethanol which would normally be encountered during ethanol fermentation processes. In operation in a vigorous environment, beads made in accordance with the present invention may remain viable for one month. Most calcium-alginate-yeast beads, common in the prior art, would dissolve or rupture in three to five days.

Beads made in accordance with the present invention can be stored in a 1% calcium chloride solution or even tap water in a closed container at moderately cool temperatures. PEI effectively prevents rotting with the exception of fungi. If stored at 4° C., beads of the present invention will store indefinitely.

In order to disclose more clearly the features and advantages of the present invention, the following summary of experimental examples illustrating the invention is given. It should be understood, however, that the summary is done solely by way of example and is intended neither to delineate the scope of the invention nor limit the ambit of the appended claims. The present invention will be discussed in terms of a biocatalyst system for the production of ethanol with the understanding that the present invention has applications in other bioconversion systems as well.

EXAMPLE I

The PEI referred to in the following discussion was obtained from the Aldrich Chemical Company of Milwaukee, Wisconsin. The PEI utilized was of an average molecular weight between 50,000 and 100,000 grams per mole. The yeast used in the following discussion was a dehydrated Baker's yeast obtained from Universal Food Corporation of Milwaukee, Wisconsin. The sodium alginate was derived from *Macrocystis pyrifera*, Type IV, obtained from the Sigma Chemical Company of St. Louis, Missouri. The surfactants include dioctyl sodium sulfosuccinate, marketed under the trade name of Triton GR-7M, and sorbitan monooleate, marketed under the trade name of Span 80. The corn oil referred to was of food grade. The kerosene was marketed under the designation F-158301 by Quimasx, Inc. of Lemont, Illinois. All inorganic substances, including calcium chloride, were of analytical grade.

Dehydrated Baker's yeast was rehydrated with distilled water to make 150 ml of a 20% yeast slurry and kept at 4° C. for one to two hours prior to use. A 2% sodium-alginate dispersion was prepared in a Waring blender, and the pH of the dispersion adjusted to 7.0. The alginate dispersion was kept in an airtight container to prevent gel thickening by carbon dioxide absorption. A 0.3 ml aliquot of 50% PEI aqueous solution was dispersed homogeneously into the 150 ml of the 2% sodium alginate dispersion by vigorously mixing in the Waring blender.

Vigorous mixing was necessary to prevent local alginate precipitation caused by the PEI. The PEI-alginate dispersion had a resultant PEI concentration of approximately 0.1%. The PEI-alginate dispersion was combined with the yeast suspension and adjusted with additional water to produce 300 ml of a yeast-polymer dispersion comprised of:

| Yeast (dry weight) | 30 g |
| Sodium alginate | 3.0 g |
| PEI | 0.15 g |
| Water | 266.8 g |

The order of mixing alginate, PEI, and yeast is important. PEI is normally toxic to yeast due to its charged nature. Mixing the PEI with alginate prior to combining with the yeast neutralizes the toxic effects of PEI.

A single-stage pelletizing apparatus was assembled which included a two-liter round flask, an overhead mixer with a half-moon shape blade and a variable autotransformer. With gentle agitation, 400 ml of corn oil and 200 ml of kerosene were introduced into the flask. Between 1 and 15 ml of the oil phase surfactant were introduced into the flask and mixed with gentle agitation. Three hundred milliliters of the yeast-polymer dispersion were added to the oil phase within the flask. With continued gentle agitation, the yeast-polymer dispersion further dispersed within the oil phase, and after 5 to 10 minutes the yeast-polymer dispersion formed tiny bead-like spheres.

Fine calcium chloride powder was prepared and 7 to 50 grams were added to the pelletization flask. The curing was maintained for 10 to 20 minutes under agitation until the beads became completely gelled. The fine calcium chloride powder acts as a matrix gelling agent, an anti-adhering agent, and a dehydration agent. When calcium chloride powder is replaced by calcium chloride solution, the yeast-polymer dispersion rapidly coagulates and sinks to the bottom of the container forming a thick viscous batter. The calcium powder protected the individual beads from adhering to one another until the individual bead surfaces became completely hardened.

The amount of calcium chloride powder added to the pelletization bath determined the degree of dehydration of the resulting beads. Where the total solid contents of the two different batches of beads, being the sum of calcium alginate and dry yeast added to each batch, remained constant, 10 g of calcium chloride powder yielded approximately 150 g of beads, whereas only 90 g of beads were obtained when the calcium chloride was increased to 40 g.

As soon as the agitation had stopped, the yeast beads and aqueous solution separated from the floating oil phase. The beads were harvested and washed with water. The calcium chloride powder dissolved in the bead-making process. Insoluble anti-adhering agents, such as bentonite or talcum powder, will contaminate the beads and will be incorporated into the bead matrix. The beads formed with calcium chloride powder were smooth and spheeical.

Aluminum sulfate may be used in conjunction with or as a replacement for calcium chloride as a gelling, anti-adhering, and dehydration agent. However, the use of aluminum sulfate resulted in beads which have a lumpy or textured appearance. Other multivalent cation salts of Group II or Group III metals which are also water soluble and oil insoluble could also be used; however, many are considered toxic and may reduce the potency or activity of the cells immobilized within the beads.

Surfactants play a decisive role in determining the size of the resulting beads. A very wide range of bead sizes, 20 microns to 1500 microns, can be obtained using in combination or separately two surfactants, dioctyl sodium sulfosuccinate and sorbitan monooleate, in different ratios. Thus, combining 16 g of dioctyl sodium sulfosuccinate per liter of oil phase and omitting the sorbitan monooleate produced beads having a diameter of 20 microns. Utilizing 1.0 g of sorbitan monooleate per liter of oil phase and omitting the dioctyl sodium sulfosuccinate produced beads having a median bead diameter of 1500 microns. The following Table I summarizes the surfactant formulation which was employed for various bead sizes.

TABLE I

| Median bead diameter (in microns) | Surfactant formulation (g/l in oil phase) |
|---|---|
| 20 | DSS 16 |
|  | SM 0 |
| 70 | DSS 10 |
|  | SM 25 |
| 150 | DSS 5 |
|  | SM 25 |
| 250 | DSS 2 |
|  | SM 17 |
| 500 | DSS 0 |
|  | SM 17 |
| 1500 | DSS 0 |
|  | SM 1 |

A screen analysis of the PEI-alginate-yeast beads formed in the presence of sodium monooleate in a concentration of approximately 1 g/l oil phase and 10.0 g calcium chloride revealed a narrow range of bead sizes as set forth below in Table II.

TABLE II

| U.S. standard mesh no. | Bead diameter | Yield from 300 g slurry | % |
|---|---|---|---|
| >12 | >1.7 mm | 4.5 g | 3 |
| 12-24 | 0.7-1.7 mm | 135.1 g | 92 |
| 24-48 | 0.3-0.7 mm | 7.4 g | 5 |
| <48 | <0.3 mm | 0 g | 0 |
| Total |  | 147.0 g | 100 |

A yield of 147.0 g beads was obtained from 300 ml of the yeast-polymer mixture.

It should be noted that in the absence of PEI the yeast-alginate dispersion is extremely difficult to control during the bead forming process due to adhesions. The resulting bead-like structures are irregular, fibrous, or adhere in clumps. A screen analysis of a calcium-alginate matrix (in the absence of PEI) revealed a wide range of bead sizes as set forth below in Table III.

TABLE III

| U.S. standard mesh no. | Bead diameter | Yield from 300 g slurry | % |
|---|---|---|---|
| >12 | >1.7 mm | 55.5 g | 37 |
| 12-24 | 0.7-1.7 mm | 39.0 g | 26 |
| 24-48 | 0.3-0.7 mm | 33.1 g | 22 |
| <48 | <0.3 mm | 22.4 g | 15 |
| Total |  | 150.0 g | 100 |

Whereas 92% of the beads formed in the PEI modified polymer-yeast compositions fell within a narrow range of 0.7 to 1.7 mm, the alginate-yeast composition, which was unmodified with PEI, had a wide dispersion extending from less than 0.3 to greater than 1.7 mm.

Beads larger than 1500 microns were made by adjusting the pH of the PEI, alginate, and yeast dispersion during the gelling process. For large beads, ranging in size from 0.5 to 3.0 mm in diameter, the pH of the PEI, alginate, and yeast mixture was maintained at 7.5 to 8.0 and above in order to prevent premature gelling by cations. Gel formation was triggered after mixing the PEI, alginate, and yeast dispersion in the oil phase, under gentle agitation, by lowering the pH of the dispersion in the oil phase to approximately 6.

Care must be taken that the pH does not remain elevated for prolonged periods of time. Generally, yeast and other microorganisms will not remain viable if subjected to extended periods where pH is elevated above 8 or depressed below 6.

Surfactants play a smaller role in controlling bead formation as bead size increases. Thus, beads having diameters of 0.5 mm were formed where the concentration of the sole surfactant, sorbitan monooleate, was 17 grams per liter in the oil phase, beads of 1.5 mm were formed where the concentration of the sole surfactant, sorbitan monooleate, was 1.0 gram per liter. For beads having a diameter of 2.0 mm, the surfactant sorbitan monooleate was present in only trace amounts and for beads of 3.0 mm was omitted entirely. It will be recognized by those skilled in the art that other surfactants may be substituted for sorbitan monooleate and dioctyl sodium sulfosuccinate. EXAMPLE II The present bead composition of alginate, PEI, and yeast can withstand the harsh conditions where vigorous gas actions, high alcohol concentrations, and digestive enzymes prevail. The beads allow the growth of yeast by expanding and allow internally generated carbon dioxide to be effectively transported out of the bead without internal damage.

Thus, films of PEI and alginate having 10 parts per hundred (pph) PEI and a mean cross-sectional area of 0.0087 $in^2$ have a mean tensile strength of 104.3 pounds per square inch (psi) and a means ultimate elongation of 98.0%. Calcium alginate gel films of twice the thickness, 0.0177 in $^2$, only demonstrate a mean tensile strength of 83.7 psi and a means ultimate elongation of 79.3%.

Combined with yeast, PEI-alginate-yeast gel films, having 10 pph and a mean cross-sectional area of 0.011 $in^2$ have a means tensile strength of 17.6 psi and a mean ultimate elongation of 55.3%. In comparison, yeast-calcium-alginate gel films having almost three times the thickness, approximately 0.032 $in^2$, demonstrate a mean tensile strength of only 10.4 psi and a means ultimate elongation of approximately 59.7%.

After fermentation, PEI-alginate-yeast gel films continue to demonstrate surprising and expected strength and resiliency. PEI-alginate-yeast films after fermentation and having a means thickness of 0.04 in $^2$, demonstrate a mean tensile strength of approximately 6.2 psi and a means ultimate elongation of 24%. In comparison, yeast-calcium-alginate gel films after fermenetation and having a much greater thickness, averaging 0.064 in$^2$, have a mean tensile strength of only about 3.9 psi and a mean ultimate elongation of only 22.3%.

Despite non-sterile conditions, the PEI is effective in curtailing bacterial growth. Thus, *Escherichia coli* cells immobilized in gelatin, agar or alginate in the presence of 10 pph PEI, incubated at 35° C. for ten days in 0.1 molar glycine buffers at a pH of 7 and 9 and containing minerals and nutrients exhibit no growth. In contrast, the same carrier materials without PEI all exhibit heavy growth of *Escherichia coli*.

EXAMPLE III

The beads of the present invention are well-suited for ethanol fermentation either in batch fermentation processes or within packed columns. In the following discussions, the mediums for yeast fermentation included alpha-D-glucose derived from core hydrolysates containing approximately 5% of beta-D-glucose obtained from the Sigma Chemical Company of St. Louis, Mo. The YM broth was obtained from Difco Laboratories of Detroit, Mich. Vitamins and yeast extract were obtained from the Sigma Chemical Company, and all inorganic chemicals referred to are of analytical grade.

Glucose media having different formulations were prepared and transferred to fermentation flasks in 50 ml aliquots. Each media contained 13% glucose. The first medium, identified below as a tap water medium, contained only 13% glucose in tap water. A second 13% glucose medium formulation, identified as an organic medium, also included 2% YM broth, 0.3% yeast extract, $(NH_4)_2SO_4$ at 1 g/l, $KH_2PO_4$ at 0.2 g/l, $MgSO_4.7H_2O$ at 1.2 g/l, and $CaCl_2.2H_2O$ at 0.74 g/l. A third medium, identified below as N-medium, was nitrogen deficient including, in addition to 13% glucose, only the components $MgSO_4.7H_2O$ at 1.2 g/l, $Kh_2PO_4$ at 0.2 g/l and $Cacl_2.2H_22H_2O$ at 0.74 g/l. A fourth medium, identified below as PK-medium, was potassium and phosphate deficient including, in addition to 13% glucose, only $(NH_4)_2SO_4$ at 1 g/l and $MgSO_4.7H_2O$ at 1.2 g/l. A still fifth medium, identified below as Mg-medium, was magnesium deficient including, in addition to 13% glucose, only $KH_2PO_4$ at 0.2 g/l, $(NH_4)_2SO_4$ at 1 g/l, and $CaCl_2.2H_2O$ at 0.74 g/l.

The flasks were stopped with cotton balls and autoclaved for 15 minutes at 121° C. Flasks were inoculated with 5 g of beads and designated "A" or 1.3 g of beads and designated "B". Fermentation was carrier out on a New Brunswick G10 gyratory shaker at 150 rpm. The fermentation temperatures were either 25° C. or 30° C. Samples of broth were obtained in a clean chamber and quenched with four volumes of 0.33N perchloric acid and stored at −20° C. in tightly capped containers until analyses were performed. Glucose was analyzed enzymically using Sigma Company's glucose assay vial, No. 15-10. The formation of NADPH was detected spectrophotometrically at 340 nm using a Perkin-Elmer Lambda 5 Precision Spectrophotometer. Ethanol was assayed using alcohol dehydrogenase. Formation of NADH was followed spectrophotometrically employing Sigma Chemical Company's ethanol assay vials, No. 330–5, and glycine buffer reagent, No. 332-9.

The results of the flask batch fermenetation are set forth in the table below:

TABLE IV

| Run No. | Ethanol Yield | Remarks |
|---|---|---|
| 1-A | 45.0 g/l | Tap water |
| 1-B | 1.0 g/l | |
| 2-A | 50.0 g/l | Organic medium |
| 2-B | 50.0 g/l | |
| 3-A | 45.0 g/l | N-medium |
| 3-B | 6.5 g/l | |
| 4-A | 43.0 g/l | PK-medium |
| 4-B | 1.0 g/l | |
| 5-A | 42.0 g/l | Mg-medium |
| 5-B | 4.0 g/l | |

The batch fermentation runs indicate that immobilized yeast beads were active in converting glucose to ethanol regardless of the presence or essential nutrients. When a larger amount of beads were used, all fermenetation flasks contained high concentrations of ethanol irrespective of the medium. When the beads were reduced by one-fourth, only complete organic mediums could produce the same amount of ethanol compared to the control. In a long-term three-day fermentation, a complete nutrient formulation was necessary for high ethanol yield; however, in time the complete nutrient formulation caused excessive growth of yeast within the bead matrix which was detrimental to overall ethanol yields.

EXAMPLE IV

Continuous ethanol fermentation was carried out in a packed column apparatus. A glass fermenter column, having approximate dimensions of 26 mm ×40 cm, was filled three-quarters full with approximately 60 grams of PEI-alginate-yeast beads, 0.7 to 1.7 mm in diameter, to form a catalyst bed. The beads floated upward against a support screen which allowed the fermented broth and fermented gas to be separated in a glass liquid separator located on the top of the fermenter column. Sterile medium was continuously fed from a reservoir to the bottom of the column upward via a peristaltic feed pump. Air was injected in the medium stream at a continuous rate of 400 ml/hr at standard temperature and pressure via an air injection pump. a sump pump drained the fermented broth continuously into a product reservoir. The medium reservoir, air injection pump inlet, column gas outlet, and product reservoir were protected with bacterial filters but the column and catalyst beads were not sterilized. A liquid level approximately 2 cm above the catalyst bed was maintained.

The beads activated for one to two days by eluting the fermentation medium at a rate of 50 ml/hr. The fermentation medium is set forth in Table V below.

TABLE V

| Chemical | Concentration (per liter) |
|---|---|
| Glucose | 170 g |
| Peptone | 5 g |
| Yeast extract | 6 g |
| Malt extract | 3 g |
| $(NH_4)_2SO_4$ | 1 g |
| $KH_2PO_4$ | 0.5 g |
| $CaCl_2.2H_2O$ | 0.7 g |
| $MgSO_4.7H_2O$ | 1.2 g |
| $ZnSO_4.7H_2O$ | 1 mg |
| $MnSO_4.1H_2O$ | 1 mg |
| $FeCl_3.6H_2O$ | 1 mg/l |
| $NaMoO_4.2H_2O$ | 0.3 mg |
| $CoCl_2.6H_2O$ | 0.3 mg |
| $H_3BO_3$ | 0.3 mg |

TABLE V-continued

| Chemical | Concentration (per liter) |
| --- | --- |
| $CuSO_4.5H_2O$ | 0.1 mg |
| Biotin | 0.05 mg |
| Pantothenate | 1.5 mg |
| Folic acid | 2.5 mg |
| Inositol | 4 mg |
| Niacin | 1 mg |
| P-Aminobenzoic acid | 2.5 mg |
| Pyridoxine | 1 mg |
| Riboflavin | 0.25 mg |
| Thiamine | 1 mg |

As the beads became activated, the size of the beads increased two- to threefold by weight, and the density of the beads decreased due to vigorous $CO_2$ generation inside the beads. The fully activated beads formed a compact bed in the upper section of the column with well-developed gas channels. The bead packing density ranged from 0.45 to 0.55 g beads/cm$^3$ bed volume. The bed volume remained steady after the initial rapid increase during the activation period. After activation, the flow rate of the medium was controlled and the column equilibrated until a steady ethanol concentration was obtained in the effluent broth before samples were taken. Samples were taken at different space velocities, and the fermenter was operated under isothermal conditions at 22° C. The fermented broth samples were quenched with 0.33N perchloric acid and evaluated as described previously.

The performance of the PEI-alginate-yeast beads in a column reactor apparatus is summarized in FIG. 1. The circled points depict productivity in grams of ethanol per liter per hour. The squared points depict ethanol concentration as a percentage of the fermentation medium. The points surrounded by triangular forms depict residual sugar concentration as a percentage of the fermentation medium. The open forms depict the performance of PEI-alginate-yeast beads of the present invention. The solid filled forms depict the performance of calcium-alginate-yeast beads.

The data depicted in the graphs is based on the analysis of the fermented broth. No correction for ethanol loss in the gas stream was made. The highest production rate of 84 g/l/h was obtained at a space velocity of 1.68 h$^{-1}$ with an ethanol concentration of 50 g/l. With the correction of the ethanol loss in the gas stream, the actual production rate would be as high as 86 g/l/h based on the catalyst bed volume. The highest ethanol concentration obtained by a single pass through the reactor was 74 g/l at 0.53 h$^{-1}$ space velocity. With a gas phase correction, the value of 74 g/l is equivalent to a 7.7% ethanol concentration with an ethanol yield as high as 47% based on glucose feed.

Thus, the present PEI-alginate-yeast beads, which obtained a productivity per bed volume of 86 g/l/h, compare favorably to prior art productivity of 46 g/l/h using calcium alginate to immobilize yeast claimed by T. Shiotani and T. Yamane in the article referred to earlier in the application. The superiority of the present invention is due to the uniformity of the beads and the ability of the beads to retain their structure during the fermentation process. Thus, the present PEI-alginate-yeast carrier matrix provides greater catalyst potency and stability, mechanical strength and resiliency, improved yeast cell retention in the beads, and increased ethanol yields.

The alginate-PEI reaction in forming the matrix neutralizes the toxic effects of PEI on yeast, such that there is no detrimental effect on ethanol production in PEI-alginate matrixes compared to calcium-alginate matrixes. In fact, incorporation of pEI into the alginate matrix resulted in increased ethanol yields. As much as a 10% increase in ethanol yield was observed with a shaker flask fermentation process when 10 pph PEI was incorporated in the alginate matrix, as set forth in Table VI.

TABLE VI

| PEI content (pph of Na-alginate) | Ethanol yield (g/l) |
| --- | --- |
| 0 | 57 |
| 1.1 | 58 |
| 3.3 | 61 |
| 10 | 63 |
| 30 | 63 |

Moreover, calcium alginate itself cannot withstand stresses caused by vigorous carbon dioxide generation, cell proliferation, and the digestive environment during high rate ethanol fermentation. Unmodified calcium-alginate beads ruptured and severely shrunk due to the loss of cells and the dissolved matrix. Unmodified calcium alginate beads resulted in as much as 70% bed shrinkage in a 4-day trial whereas the PEI modified alginate beads of the present invention allow cell growth by elastic expansion, and can withstand the harsh fermentation environment maintaining consistent bed volume after the initial rapid growth of the beads from two- to threefold by weight. The free cell washout in the PEI modified alginate-yeast beads was less than 1 g/l (or $4 \times 10^7$ cells/cc) on a dry weight basis, approximately 1/15 of the cell washout rate for a typical free cell continuous fermenter.

In spite of the non-sterile system, the continuous fermentation process did not experience bacterial proliferation under any circumstances. This is attributed to the low pH fermentation conditions and the bacteriostatic effect of PEI. PEI causes lysis of certain bacteria which greatly aids in the maintenance of an aseptic fermentation process.

The present PEI modified alginate-yeast beads could withstand vigorous gas action in the digestive environment of an alcohol fermenter. PEI modified alginate beads have potential for widespread use in the bioconversion industry including organic acid production. Use of the present invention could result in significant savings in capital and operating costs as well as result in improved yields.

Thus, while preferred embodiments have been illustrated and described, it is understood that the present invention is capable of variation and modification and, therefore, should not be limited to the precise details set forth, but should include such changes and alterations as fall within the purview of the following claims.

What is claimed is:

1. A method of making a biocatalyst system which comprises the steps of:
   mixing a biocatalytic entity with the reaction product of a homogeneous dispersion of an anionic polysaccharide polymer with a cationic polymer to form a polymer-biocatalyst dispersion;
   mixing said polymer biocatalyst dispersion with an oil phase to form beads, and mixing a powder with the beads in the oil phase wherein the powder comprises a water soluble and oil insoluble multivalent cation salt and said powder acts to gell and dehydrate the beads and to prevent the beads from adhering to one another until individual bead surfaces become hardened whereby said biocatalyst system is provided aim.

2. The method of claim 1 wherein said powder is selected from the group consisting of calcium chloride and aluminum sulfate.

3. The method of claim 1 wherein said anionic polysaccharide polymer is an anionic form of alginate.

4. The method of claim 1 wherein said cationic polymer is selected from the group including polyalkane amines and imines.

5. The method of claim 1 wherein said cationic polymer is polyethyleneimine.

6. The method of claim 1 wherein said biocatalytic entity is a microorganism.

7. The method of claim 6 wherein said microorganism is a yeast.

8. The method of claim 1 wherein said step of mixing said polymer biocatalyst dispersion with an oil phase is performed in the presence of surfactants.

9. The method of claim 1 wherein said polymer biocatalyst dispersion has a pH and said pH is altered causing the dispersion to gel.

10. The method of claim 9 wherein the pH of the polymer biocatalyst dispersion is above approximately 7.5 and lowered after mixing with the oil phase to approximately 6.

11. The method of claim 8 wherein said surfactants are selected from the group consisting of water insoluble surfactants and water soluble surfactants.

12. The method of claim 11 wherein the relative amounts of water insoluble surfactants and water soluble surfactants are varied to adjust bead size.

13. The method of claim 1 wherein the biocatalyst system prepared is used to produce ethanol by contacting the system with a fermentable substrate and recovering ethanol therefrom.

14. The method of claim 13 wherein said polysaccharide polymer is an anionic form of alginate.

15. The method of claim 13 wherein said cationic polymer is polyethyleneimine.

16. The method of claim 13 wherein said biocatalytic entity is a microorganism.

17. The method of claim 13 wherein said mixing of said polymer biocatalyst dispersion with an oil phase is performed in the presence of surfactants.

18. A biocatalyst system prepared by the method of claim 1.

19. A method of making a biocatalyst system which comprises the steps of:
mixing a biocatalytic entity with the reaction product of a homogeneous dispersion of an anionic polysaccharide polymer with a cationic polymer to form a polymer-biocatalyst dispersion, said cationic polymer selected from the group consisting of polyalkane amines and imines;
mixing said polymer-biocatalyst dispersion with an oil phase to form beads; and
adding a powder to the beads in said oil phase wherein said powder includes water soluble and oil insoluble salts having multivalent cations, and said powder acts to gell and dehydrate the beads and to prevent the beds from adhering to one another until individual bead surfaces become hardened whereby said biocatalyst system is provided.

* * * * *

UNITED STATES PATENT AND TRADEMARK OFFICE
CERTIFICATE OF CORRECTION

PATENT NO. : 4,996,150

DATED : February 26, 1991

INVENTOR(S) : Joung, et al.

It is certified that error appears in the above-identified patent and that said Letters Patent is hereby corrected as shown below:

On the title page,
item [57] ABSTRACT  Line
                              7         "surtactant" should read --surfactant--.
                            11        "gell" should read --gel--.

| Col. | Line | |
|---|---|---|
| 2 | 60 | "Crah" should read --Crab--. |
| 7 | 3 | "spheeical" should read --spherical--. |
| 8 | 43 | "Example II" should be deleted and inserted at line 44 as a separate line. |
| 8 | 54 | "means" should read --mean--. |
| 8 | 56 | "in $^2$" should read --in$^2$--. |
| 8 | 56 | "means" should read --mean--. |
| 8 | 61 | "means" should read --mean--. |
| 8 | 65 | "means" should read --mean--. |
| 9 | 2 | "means" should read --mean--. |
| 9 | 4 | "means" should read --mean--. |
| 9 | 42 | "Kh$_2$PO$_4$" should read --KH$_2$PO$_4$--. |
| 9 | 43 | "Cacl$_2$" should read --CaCl$_2$--. |
| 9 | 43 | "2H$_2$2H$_2$O" should read --2H$_2$O--. |
| 9 | 54 | "carrier" should read --carried--. |
| 10 | 1 | "fermenetation" should read --fermentation--. |

UNITED STATES PATENT AND TRADEMARK OFFICE
CERTIFICATE OF CORRECTION

PATENT NO. : 4,996,150

DATED : February 26, 1991

INVENTOR(S) : Joung, et al.

It is certified that error appears in the above-identified patent and that said Letters Patent is hereby corrected as shown below:

| Col. | Line | |
|---|---|---|
| 10 | 18 | "or" should read --of--. |
| 10 | 19-20 | "fermenetation should read --fermentation--. |
| 10 | 45 | "pump. a" should read --pump. A--. |
| 12 | 3 | "pEI" should read --PEI--. |
| 12 | 68 | "gell" should read --gel--. |
| 13 | 5 | "aim." should read --.--. |
| 14 | 32 | "gell" should read --gel--. |
| 14 | 33 | "beds" should read --beads--. |

Signed and Sealed this

Twenty-fifth Day of August, 1992

Attest:

DOUGLAS B. COMER

*Attesting Officer*　　　*Acting Commissioner of Patents and Trademarks*